US011887170B1

(12) United States Patent
Hallo et al.

(10) Patent No.: US 11,887,170 B1
(45) Date of Patent: Jan. 30, 2024

(54) MEDICAL PROCEDURE CHARGE RESTRUCTURING TOOLS AND TECHNIQUES

(71) Applicant: MedCom Solutions, Inc., Pittsburgh, PA (US)

(72) Inventors: Carlee Hallo, Pittsburgh, PA (US); Rebecca Mumford, Pittsburgh, PA (US); Ziwei Yi, Pittsburgh, PA (US); Nike Cromes, Pittsburgh, PA (US); William A. Hunt, Pittsburgh, PA (US)

(73) Assignee: MedCom Solutions, Inc., Pittsburgh, PA (US)

( * ) Notice: Subject to any disclaimer, the term of this patent is extended or adjusted under 35 U.S.C. 154(b) by 0 days.

(21) Appl. No.: 16/508,795

(22) Filed: Jul. 11, 2019

Related U.S. Application Data

(60) Provisional application No. 62/696,520, filed on Jul. 11, 2018.

(51) Int. Cl.
   *G06Q 30/0283*   (2023.01)
   *G16H 20/40*   (2018.01)

(52) U.S. Cl.
   CPC ......... *G06Q 30/0283* (2013.01); *G16H 20/40* (2018.01)

(58) Field of Classification Search
   CPC ........... G06Q 30/0283; G06Q 10/0633; G06Q 50/22; G06Q 50/24; G16H 20/40;
   (Continued)

(56) References Cited

U.S. PATENT DOCUMENTS 5,018,067 A * 5/1991 Mohlenbrock ........ G16H 40/20
                                                    600/300
5,325,293 A     6/1994 Dorne
                  (Continued)

FOREIGN PATENT DOCUMENTS

WO       0193067 A1    12/2001
WO       0210961 A2     2/2002
WO    2005059685 A2     6/2005

OTHER PUBLICATIONS

A. Cortes, A. Ripoll, M.A. Senar, E. Luque, Dynamic Load Balancing Strategy for Scalable Parallel Systems, 1998 (Year: 1998).*
(Continued)

*Primary Examiner* — Rachelle L Reichert
*Assistant Examiner* — Shyam M Goswami
(74) *Attorney, Agent, or Firm* — Leech Tishman Fuscaldo & Lampl, LLC; Michael D. Lazzara

(57) ABSTRACT

Computer-implemented tools, techniques, and algorithms are provided for meeting financial targets in connection with medical procedures (e.g., surgical operations) performed by a healthcare entity. A method for restructuring classification of multiple medical procedures for a healthcare entity may be provided in which medical procedure data including charge related data are collected in association with multiple patient encounters for a medical procedure. A data model is created from the collected data and a predetermined number of procedure charge levels are generated each in association with an acuity resource value range. Each medical procedure is then reclassified into one of the procedure charge levels in accordance with at least one level assignment rule. This reclassification can then be processed to determine whether it results in a predetermined desired data distribution and/or meets financial targets for the medical procedure charge data.

20 Claims, 12 Drawing Sheets

(58) Field of Classification Search
CPC ........ G16H 30/20; G16H 40/20; G16H 50/20;
G16H 10/60; G06N 5/022; G06F
16/24578; G06F 19/30; G06F 19/32;
G06F 19/34; G06F 19/36
See application file for complete search history.

(56) References Cited

U.S. PATENT DOCUMENTS

| | | | |
|---|---|---|---|
| 5,729,735 A | 3/1998 | Meyering | |
| 5,794,220 A | 8/1998 | Hunt | |
| 5,852,715 A | 12/1998 | Raz et al. | |
| 5,873,069 A | 2/1999 | Reuhl et al. | |
| 5,960,407 A | 9/1999 | Vivona | |
| 5,987,425 A | 11/1999 | Hartman et al. | |
| 6,266,655 B1 | 7/2001 | Kalyan | |
| 6,507,822 B1 | 1/2003 | Walker et al. | |
| 6,826,538 B1 | 11/2004 | Kalyan et al. | |
| 6,850,903 B2 | 2/2005 | Levine | |
| 6,910,017 B1 | 6/2005 | Woo et al. | |
| 6,965,867 B1 | 11/2005 | Jameson | |
| 7,010,494 B2 | 3/2006 | Etzioni et al. | |
| 7,020,617 B2 | 3/2006 | Ouimet | |
| 7,062,447 B1 | 6/2006 | Valentine et al. | |
| 7,346,522 B1 | 3/2008 | Baylor et al. | |
| 7,565,300 B2 | 7/2009 | Hunt et al. | |
| 8,073,709 B2 | 12/2011 | Moreno et al. | |
| 8,103,541 B2 | 1/2012 | Abrams | |
| 8,615,403 B2 | 12/2013 | Lipsky et al. | |
| 10,467,383 B2 * | 11/2019 | Dettinger | A61B 5/4833 |
| 2001/0032196 A1 | 10/2001 | Krespi | |
| 2002/0004789 A1 | 1/2002 | Huyler | |
| 2002/0026368 A1 | 2/2002 | Carter | |
| 2002/0046128 A1 | 4/2002 | Abe et al. | |
| 2002/0065717 A1 | 5/2002 | Miller et al. | |
| 2002/0072956 A1 | 6/2002 | Willems et al. | |
| 2002/0073051 A1 | 6/2002 | Blouin et al. | |
| 2002/0095327 A1 | 7/2002 | Zumel et al. | |
| 2002/0099596 A1 | 7/2002 | Geraghty | |
| 2002/0116348 A1 | 8/2002 | Phillips et al. | |
| 2002/0165834 A1 | 11/2002 | Delurgio et al. | |
| 2002/0178109 A1 | 11/2002 | Bye | |
| 2002/0188576 A1 | 12/2002 | Peterson et al. | |
| 2002/0194143 A1 | 12/2002 | Banerjee et al. | |
| 2003/0110066 A1 | 6/2003 | Walser et al. | |
| 2003/0120579 A1 | 6/2003 | Carter, III | |
| 2003/0126097 A1 | 7/2003 | Zhang et al. | |
| 2003/0149709 A1 | 8/2003 | Banks | |
| 2003/0177103 A1 | 9/2003 | Ivanov et al. | |
| 2003/0200185 A1 | 10/2003 | Huerta et al. | |
| 2003/0216946 A1 | 11/2003 | Ferraro | |
| 2003/0217016 A1 | 11/2003 | Pericle | |
| 2003/0229502 A1 | 12/2003 | Woo | |
| 2004/0024715 A1 | 2/2004 | Ouimet | |
| 2004/0049470 A1 | 3/2004 | Ouimet | |
| 2004/0068413 A1 | 4/2004 | Musgrove et al. | |
| 2004/0073520 A1 | 4/2004 | Eskandari | |
| 2004/0128163 A1 | 7/2004 | Goodman et al. | |
| 2004/0128261 A1 | 7/2004 | Olavson et al. | |
| 2004/0199417 A1 | 10/2004 | Baxter et al. | |
| 2004/0205031 A1 | 10/2004 | Cranner | |
| 2004/0243438 A1 | 12/2004 | Mintz | |
| 2004/0249769 A1 | 12/2004 | Mathews et al. | |
| 2004/0267674 A1 | 12/2004 | Feng et al. | |
| 2005/0004819 A1 | 1/2005 | Etzioni et al. | |
| 2005/0071249 A1 | 3/2005 | Nix et al. | |
| 2005/0086181 A1 | 4/2005 | Melzer | |
| 2005/0131810 A1 | 6/2005 | Garrett | |
| 2005/0149381 A1 | 7/2005 | Ravulapati et al. | |
| 2005/0149458 A1 | 7/2005 | Eglen et al. | |
| 2005/0171918 A1 | 8/2005 | Eden et al. | |
| 2005/0197971 A1 | 9/2005 | Kettner et al. | |
| 2005/0256810 A1 | 11/2005 | Lund | |
| 2005/0273415 A1 | 12/2005 | Mathews et al. | |
| 2006/0010082 A1 | 1/2006 | Gee et al. | |
| 2006/0047574 A1 | 3/2006 | Sundaram et al. | |
| 2006/0047608 A1 | 3/2006 | Davis et al. | |
| 2006/0059010 A1 | 3/2006 | Chavis-Smith et al. | |
| 2006/0080265 A1 | 4/2006 | Hinds et al. | |
| 2006/0106678 A1 | 5/2006 | Walker et al. | |
| 2006/0136264 A1 | 6/2006 | Eaton et al. | |
| 2007/0067247 A1 | 3/2007 | Brookhart | |
| 2008/0004981 A1 | 1/2008 | Gopalpur et al. | |
| 2010/0324928 A1 * | 12/2010 | Dang | G06Q 40/02 705/2 |
| 2012/0166212 A1 * | 6/2012 | Campbell | G06Q 10/10 705/2 |
| 2013/0117033 A1 * | 5/2013 | Mohlenbrock | G16H 10/60 705/2 |
| 2018/0366213 A1 * | 12/2018 | Fidone | G16H 50/20 |
| 2019/0096017 A1 * | 3/2019 | Whitley | G06Q 10/06395 |

OTHER PUBLICATIONS

Bils et al., "Understanding How Price Responds to Costs and Production", Forthcoming in Carnegie-Rochester Conference Series on Public Policy, Jul. 1999.
Breidert et al., "Reservation Price Estimation by Adaptive Conjoint Analysis".
Gerber, "Price Check: The Mystery of Hospital Pricing", Dec. 2005, California HealthCare Foundation, ISBN 1-933795-00-X.
Dennison, "Hospital Bills Sometimes Confound Even the Experts", Knight-Ridder Tribune Business News, The Montana Standard, Sep. 3, 2006.

* cited by examiner

Identification of Surgical Charges Below Reimbursement

| | | |
|---|---|---|
| Surgical Procedure: | 27446 | Revision of knee joint |
| Major Surgery: Initial 30 Mins | $ | 3,000 |
| Major Surgery: Each Additional | $ | 800 |
| X Commercial Payment: | $ | 11,134 |
| Length of Case | 135 mins | |
| Surgical Charge: | $ | 8,600 |
| Technical Anesthesia Charge: | $ | 500 |
| Recovery Charge: | $ | 1,300 |
| Total Procedure Charge: | $ 10,400 | $ 734 |

Under this scenario, for every patient with X commercial insurance, you may be leaving over $700 on the table.

FIG. 8

Current Structure:

| Level | Criteria | Init 30 Min | Each Add 15 Min |
|---|---|---|---|
| 1 | 1 staff utilized in procedure | $ 4,223 | $ 608 |
| 2 | 2 staff utilized in procedure | $ 5,255 | $ 852 |
| 3 | 3 staff utilized in procedure | $ 5,848 | $ 936 |
| 4 | 4 staff utilized in procedure | $ 6,694 | $ 1,155 |
| 5 | 5 staff utilized in procedure | $ 8,197 | $ 1,366 |

FIG. 9

Proposed Structure:

| Level | Relative Weight | Init 30 Min | Each Add 15 Min |
|---|---|---|---|
| 1 | 0.0 | $ 4,223 | $ 608 |
| 2 | 10.5 | $ 5,255 | $ 582 |
| 3 | 24.0 | $ 5,848 | $ 936 |
| 4 | 50.0 | $ 6,694 | $ 1,155 |
| 5 | 60.0 | $ 8,197 | $ 1,366 |

FIG. 10

Example of Procedure Level Change:

| Procedure | Current Level | Proposed Level |
|---|---|---|
| Remove foreign body | 2 | 1 |
| Carpal tunnel surgery | 2 | 2 |
| Cataract surgery | 2 | 3 |
| Laparoscopy appendectomy | 2 | 4 |
| Knee arthroscopy/surgery | 3 | 5 |

FIG. 11

Average Charge by Level: Current vs Proposed

| Level | Avg Chg orig | Avg Chg Rec |
|---|---|---|
| 1 | $ 11,439 | $ 10,412 |
| 2 | $ 10,556 | $ 11,114 |
| 3 | $ 12,166 | $ 13,628 |
| 4 | $ 19,248 | $ 22,880 |
| 5 | $ 24,855 | $ 32,301 |

FIG. 12

Scenario 1 - No Price Change

| | Outpatient | | | | Inpatient | | | | Total | |
|---|---|---|---|---|---|---|---|---|---|---|
| | Baseline GR | Proposed GR | Baseline Commercial Payor NR | Proposed Commercial Payor NR | Baseline GR | Proposed GR | Baseline Commercial Payor NR | Proposed Commercial Payor NR | Total GRV | GRV % | Total NRV |
| Level 1 | 15,474 | 1,565,244 | 2,814 | 311,116 | 0 | 3,038,366 | 0 | 0 | $4,588,136 | 29650% | $308,302 |
| Level 2 | 54,751,529 | 5,092,135 | 14,572,670 | 1,201,039 | 40,500,167 | 8,426,757 | 587,836 | 475,738 | ($81,732,804) | -86% | ($13,483,728) |
| Level 3 | 11,704,506 | 29,559,642 | 3,206,732 | 7,600,423 | 36,696,485 | 12,432,476 | 307,170 | 176,625 | ($6,408,874) | -13% | $4,263,146 |
| Level 4 | 90,170 | 14,588,472 | 27,860 | 4,112,361 | 6,640,961 | 14,485,207 | 94,150 | 95,534 | $22,352,548 | 332% | $4,085,886 |
| Level 5 | 0 | 23,073,603 | | 6,054,225 | 909,534 | 51,209,398 | 0 | 279,604 | $73,373,467 | 8067% | $6,333,830 |
| Level 6 | | | | | 35,971,401 | 35,992,784 | 1,931,975 | 1,937,506 | $21,384 | 0% | $5,532 |
| Total | 66,561,679 | 73,879,095 | 17,810,075 | 19,279,164 | 120,718,548 | 125,584,988 | 2,921,130 | 2,965,008 | $ 12,193,857 | 7% | 1,512,967 |

FIG. 13A

Scenario 2 - 1% Price Increase to OR Level Pricing

| | Outpatient | | | | Inpatient | | | | Total | |
|---|---|---|---|---|---|---|---|---|---|---|
| | Baseline GR | Proposed GR | Baseline Commercial Payor NR | Proposed Commercial Payor NR | Baseline GR | Proposed GR | Baseline Commercial Payor NR | Proposed Commercial Payor NR | Total GRV | GRV % | Total NRV |
| Level 1 | 15,474 | 1,573,229 | 2,834 | 311,726 | 0 | 3,042,164 | 0 | 0 | $4,599,919 | 29726% | $308,912 |
| Level 2 | 54,751,529 | 5,124,146 | 14,572,670 | 1,204,191 | 40,500,167 | 8,436,393 | 587,836 | 476,807 | ($81,691,157) | -86% | ($13,479,307) |
| Level 3 | 11,704,506 | 29,735,497 | 3,206,732 | 7,628,756 | 36,696,485 | 12,452,447 | 307,170 | 176,852 | ($6,213,047) | -13% | $4,291,706 |
| Level 4 | 90,170 | 14,664,857 | 27,860 | 4,130,588 | 6,640,961 | 14,525,640 | 94,150 | 95,950 | $22,459,366 | 334% | $4,104,529 |
| Level 5 | 0 | 23,201,646 | | 6,079,606 | 909,534 | 51,353,623 | 0 | 281,820 | $73,645,735 | 8097% | $6,361,427 |
| Level 6 | | | | | 35,971,401 | 36,080,777 | 1,931,975 | 1,948,794 | $109,376 | 0% | $16,819 |
| Total | 66,561,679 | 74,299,376 | 17,810,075 | 19,354,868 | 120,718,548 | 125,891,043 | 2,921,130 | 2,980,224 | $ 12,910,192 | 7% | 1,603,886 |

FIG. 13B

MEDICAL PROCEDURE CHARGE RESTRUCTURING TOOLS AND TECHNIQUES

CROSS REFERENCE TO RELATED APPLICATION/PRIORITY CLAIM

This non-provisional patent application claims priority to U.S. Provisional Patent Application No. 62/696,520, filed on Jul. 11, 2018, the entirety of which is hereby incorporated by reference into the present application.

FIELD OF THE INVENTION

Various embodiments of the present invention generally relate to systems, processes, devices, and techniques for analyzing different medical procedures for restructuring and reclassifying the charge process associated with the procedures. In particular embodiments, the invention may be employed in connection with analyzing and restructuring charges for surgical operations performed by a healthcare facility.

BACKGROUND

Many healthcare entities, such as hospitals, clinics, ambulatory surgery centers, medical facilities, and other healthcare providers, can benefit from customized charge cycle solutions that reduce denials, enhance revenue, improve the patient experience, and sustain accurate charging results that can lead to reduced out-of-pocket expenses for patients. In particular, healthcare entities that perform medical operations such as surgical operations could improve the accuracy and consistency of their charging practices, enhance the defensibility of their charging structures, and capture previously unrealized revenue opportunities, among other benefits. In view of these issues, more effective tools, techniques, and strategies are needed for restructuring charge processes within a healthcare entity, including enhanced control features for charges associated with medical operations performed by the entity.

BRIEF DESCRIPTION OF THE FIGURES

Various embodiments of the present invention are described with reference to the following figures, wherein like reference numerals refer to like features throughout the various views:

FIG. 8 illustrates an example of surgical charge data which is below an expected reimbursement rate for a given surgical procedure.

FIG. 9 is a table showing an example of a current structure for charging a medical procedure.

FIG. 10 is a table showing an example of a proposed structure for charging a medical procedure in connection with various relative weight ranges.

FIG. 11 is a table showing an example of changing from current to proposed procedure charge levels for various medical procedures in accordance with restructuring and reclassifying processes performed in connection with certain embodiments of the invention.

FIG. 12 is a table showing an example of average charge by assigned procedure charge level, including charges under a current structure and charges under a proposed structure recommended in accordance with certain embodiments of the invention.

FIG. 13A is a table showing an example of comparing baseline revenue to proposed revenue for various out-patient and in-patient medical procedure categories with no adjustment to pricing.

FIG. 13B is a table showing an example of comparing baseline revenue to proposed revenue for various out-patient and in-patient medical procedure categories with a 1% increase in pricing.

DESCRIPTION

Figure 1:
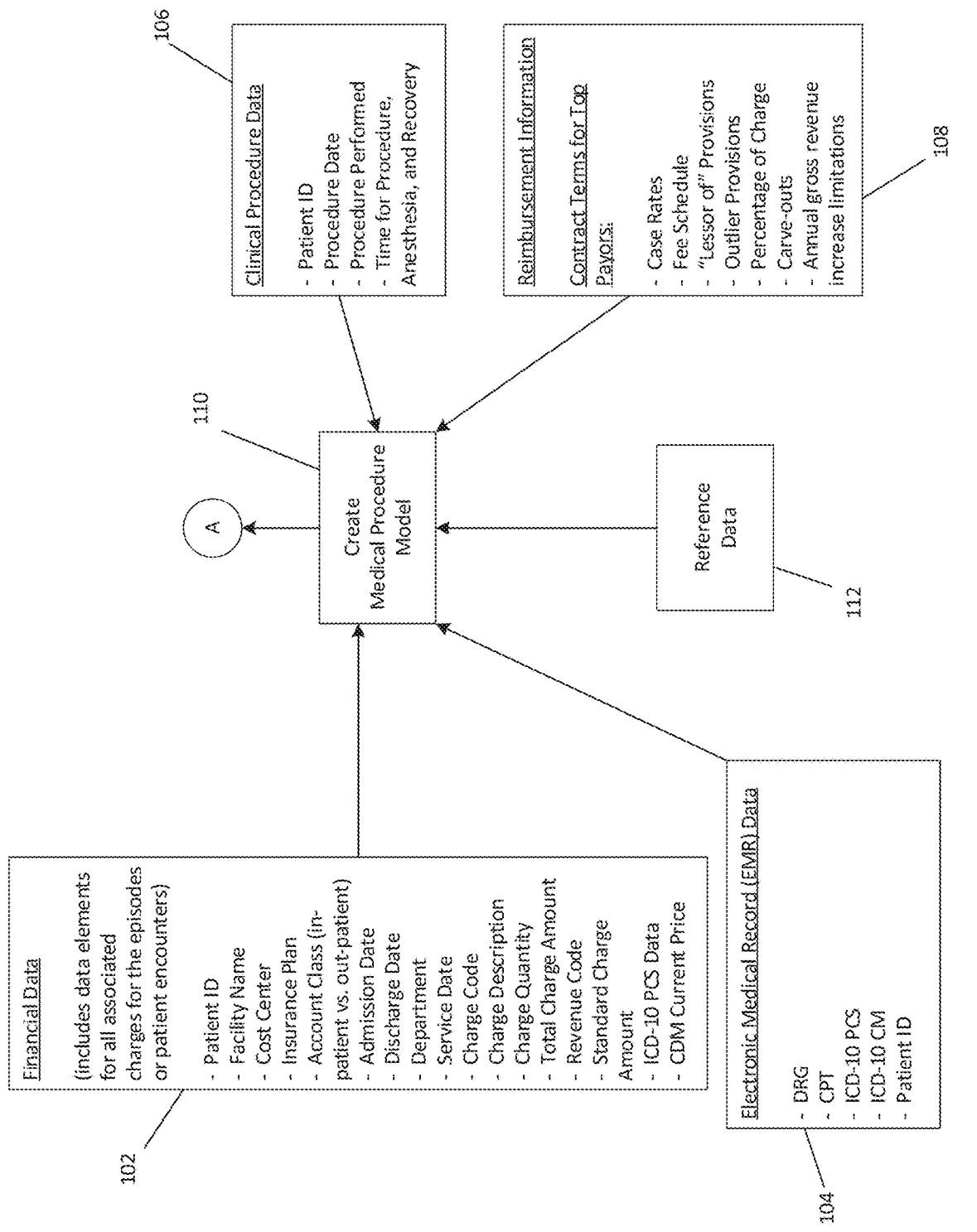
FIG. 1 schematically illustrates an example of generating a data model in connection with various sources of medical procedure related data.

In various embodiments of the present invention, computer-implemented tools, techniques, and algorithms have been developed for restructuring and reclassifying charge processes for medical procedures performed within a healthcare entity. The invention may be employed for meeting financial targets in connection with obtaining appropriate insurance reimbursement and collecting revenue derived from performing medical procedures or operations (e.g., surgical procedures) on patients. Various embodiments of the invention recognize the importance of having a healthcare system which is as fair and efficient as possible for all of its participants, especially for patients but also for healthcare professionals, medical procedure facilities, and insurance providers.

As applied herein, the term "medical procedure" includes a variety of operations, courses of treatment, and other procedures including, for example and without limitation, surgical operations, interventional radiological procedures, gastroenterological procedures, cardiology, and any other procedure that can be assigned an acuity resource value (as defined herein). It can be appreciated that even though surgical procedures are employed specifically in many of the examples described herein, the scope of various embodiments of the invention are intended to extend to many other kinds of medical procedures.

As applied herein, the term "acuity resource value" may include any value or measurement of the acuity associated with a medical procedure including, for example and without limitation, Medicare Ambulatory Payment Classification (APC) values and relative weight ranges, relative value unit (RVU) values, cost factors, reimbursement factors, or resource utilization data, among other similar types of values or measurements.

The inventors have recognized that hospitals and other medical facilities are often negatively impacted when operating rooms charge for surgical services, for example, because inconsistent or non-relevant factors may be used to classify surgical operations and their associated charges. In many cases, surgery has an ineffective number of levels of services for cases ranging from removal of a cyst to open heart surgery (e.g., from levels one to seven). Hospitals commonly use the number of nurses that are present during a surgical procedure as the determinant for the level. However, if an acute care hospital employs two nurses to participate in each procedure, then a significant portion of the procedures (e.g., over 85%) can be assigned to levels 1 and 2 (e.g., out of five possible levels) in view of the amount of nursing expertise employed. This level assignment is made regardless of the complexity and resource cost associated with these procedures, which might otherwise indicate assignment of a higher level. Incorrect assignment of a procedure charge level to a procedure correspondingly results in misstating the procedure charges, which can further result in underpayment by the insurance carrier to the hospital.

The inventors have also recognized that enhanced tools and techniques are needed to improve charge code validity, charge consistency, and charge structure within a healthcare facility's electronic charge systems. Installing accurate charge capture systems streamlines workflows and enhances the interoperability and validation of computer systems. Software tools are needed to enable facilities to gain internal control over their charge capture systems to ensure on-going management of their systems. With accurate and efficient charge capture systems and processes in place, pricing for medical operations can be aligned with the facility's strategic objectives, while reducing unnecessary audit penalties, rework, contingency fees, and associated costs. Improving charge capture efficiency can also promote capturing potential revenues within electronic charge capture systems.

In various embodiments, computer-based methods, systems, algorithms, and processes are provided for classifying medical procedures into predictable levels which are derived based a plurality of factors to reflect an intended fiscal outcome. Utilizing various digital architectural structures and databases coupled with encrypted interfaces, a data model can be generated including data related to medical procedures such as surgical procedures. The medical facility provides patient registration data, patient surgical data, patient claims data, reimbursement contractual files, protocol information, and other sources of medical procedure related data. CMS provides Ambulatory Payment Classification (APC) files and the Diagnostic Related Group (DRG). The American Medical Association provides the Current Procedural Terminology (CPT) file and CPT codes. Surgical levels of 1 to x, for example, can be used to classify the surgical procedures by acuity or charge level. Patient surgical procedures can be measured based on their APC relative weight values by using the APC numeric system. The APC relative weight ranges (e.g., 0 to 20.00 for Level 1) can be assigned to a designated number of levels. Then the method can classify each surgical procedure into one of the designated levels. Gross and net revenue can be measured, along with gross and gross net revenue variances, and if these revenue calculations do not meet a desired fiscal target, then the method may provide for adjusting the charge structure based on the APC ranges, pricing for the surgical procedure, and/or the number of surgical levels, or other factors.

FIG. 1 illustrates one example of a data collection process performed in accordance with the tools and techniques described herein. As shown, financial data 102, EMR data 104, and clinical procedure data 106 can be collected from various computer-based data sources either internal or external with respect to a healthcare entity (e.g., a hospital performing surgical operations). In certain embodiments, source data 108 associated with reimbursement information such as payor reimbursement terms, for example, can be collected as well. All or a portion of this collected data be aggregated into a medical procedure model 110 (e.g., a surgical model) which can be created for the healthcare entity. In certain embodiments, the surgical model 110 may be constructed in association with various types of reference data sources 112. Examples of data which may be obtained from the reference data sources 112 include APC relative weights published by Centers for Medicare and Medicaid Services (CMS); CPT codes, descriptions, and other data generated by the American Medical Association (AMA); as well as other kinds of data.

Figure 2:
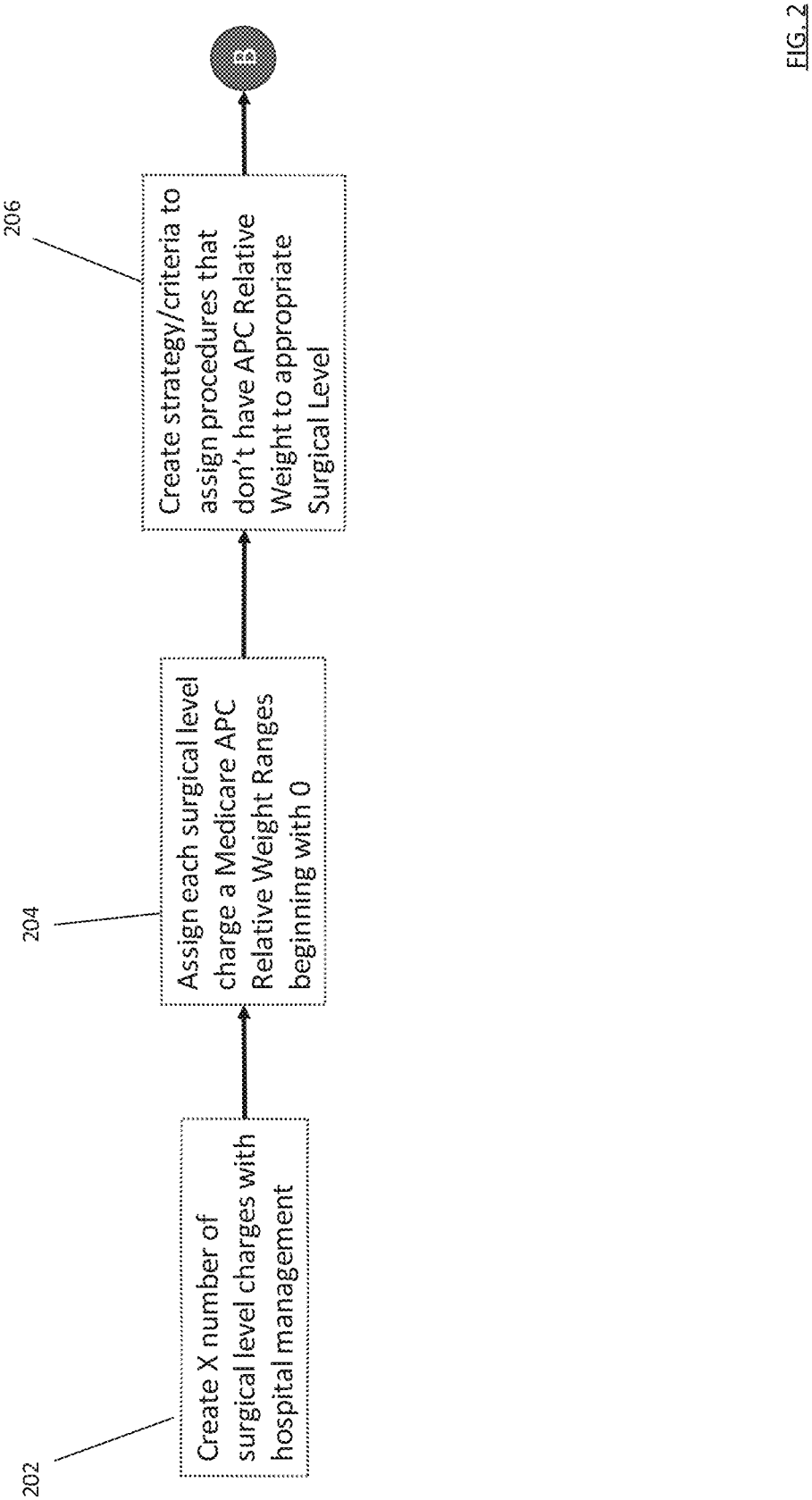
FIG. 2 is a process flow diagram illustrating one example of a process for creating a procedure charge level hierarchy.

FIG. 2 provides an example of a process for assigning surgical levels in association with creation of the surgical model 110. At step 202, a predetermined number of surgical level charges can be created, perhaps by working with management of the healthcare entity (e.g., hospital management). At step 204, each surgical level created can be assigned an acuity resource value in accordance with Medicare's APC relative weight scheme, for example. At step 206, any medical procedure that does not have a relative weight under the Medicare APC scheme can nonetheless be assigned to an appropriate surgical level. For example, in one embodiment, an inpatient only procedure without a relative weight can be automatically assigned by default to the highest surgical level.

Figure 3:
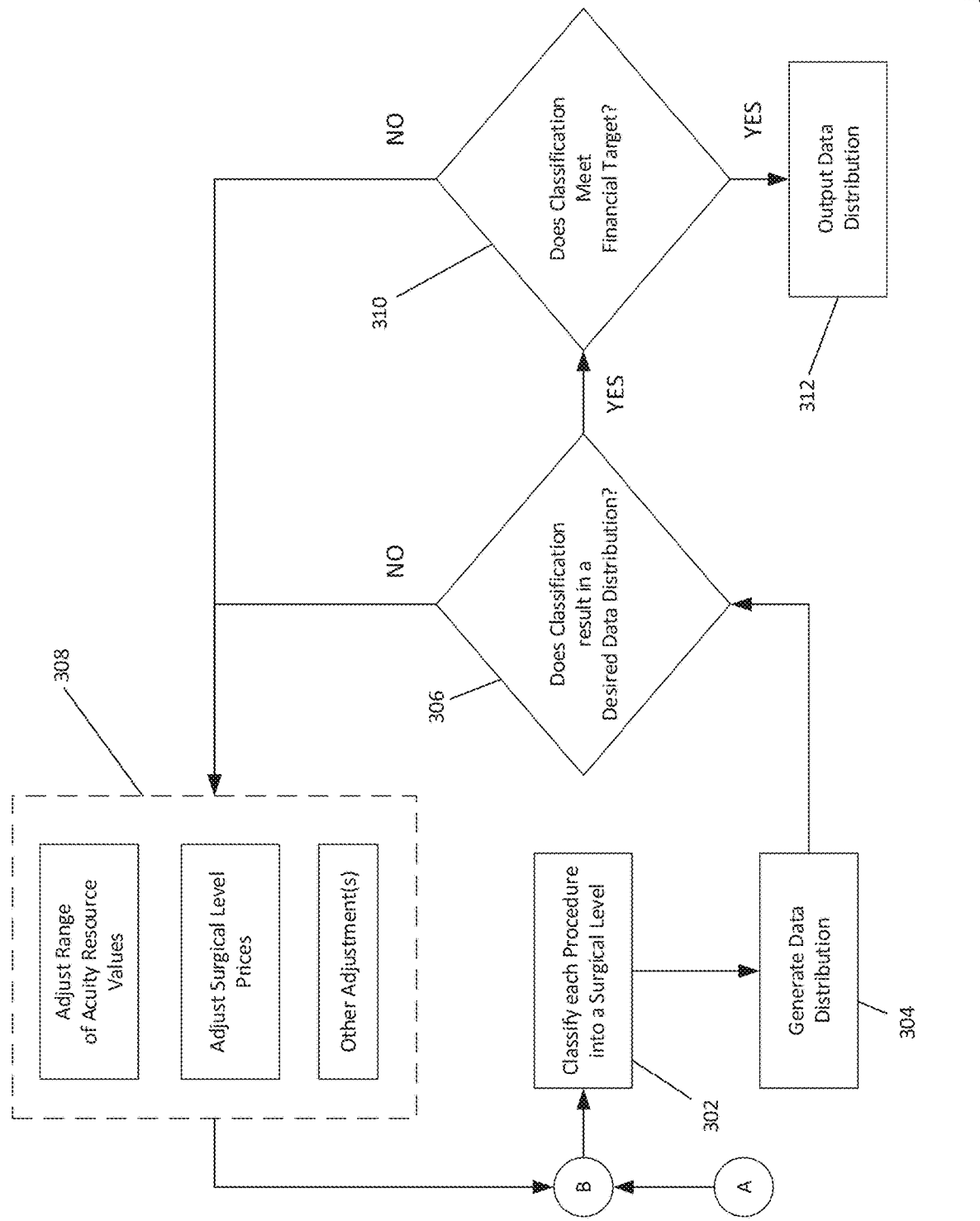
FIG. 3 is a process flow diagram illustrating one example of a process for restructuring and reclassifying medical procedure charges in accordance with certain embodiments of the invention.

FIG. 3 provides an example of a process for iteratively developing a desired data distribution for charge practices for medical procedures which meets certain targets established by a healthcare entity. At step 302, each medical procedure (e.g., surgical operation) is classified into one of the surgical levels created for the surgical model (see above). Variables affecting classification of medical procedures may include, for example and without limitation, a service mix of procedures performed by the healthcare entity, a mix of patient types, and/or a variety of other factors. At step 304, a data distribution is generated in association with the medical procedures in accordance with their classification into the different surgical levels. At step 306, a determination is made as to whether the generated data distribution results in a desirable data distribution. For example, a bell curve distribution, a curve-shifted distribution, or another kind of statistical distribution, might be desired for the classification of the medical procedures into the different surgical levels.

Figure 4A:
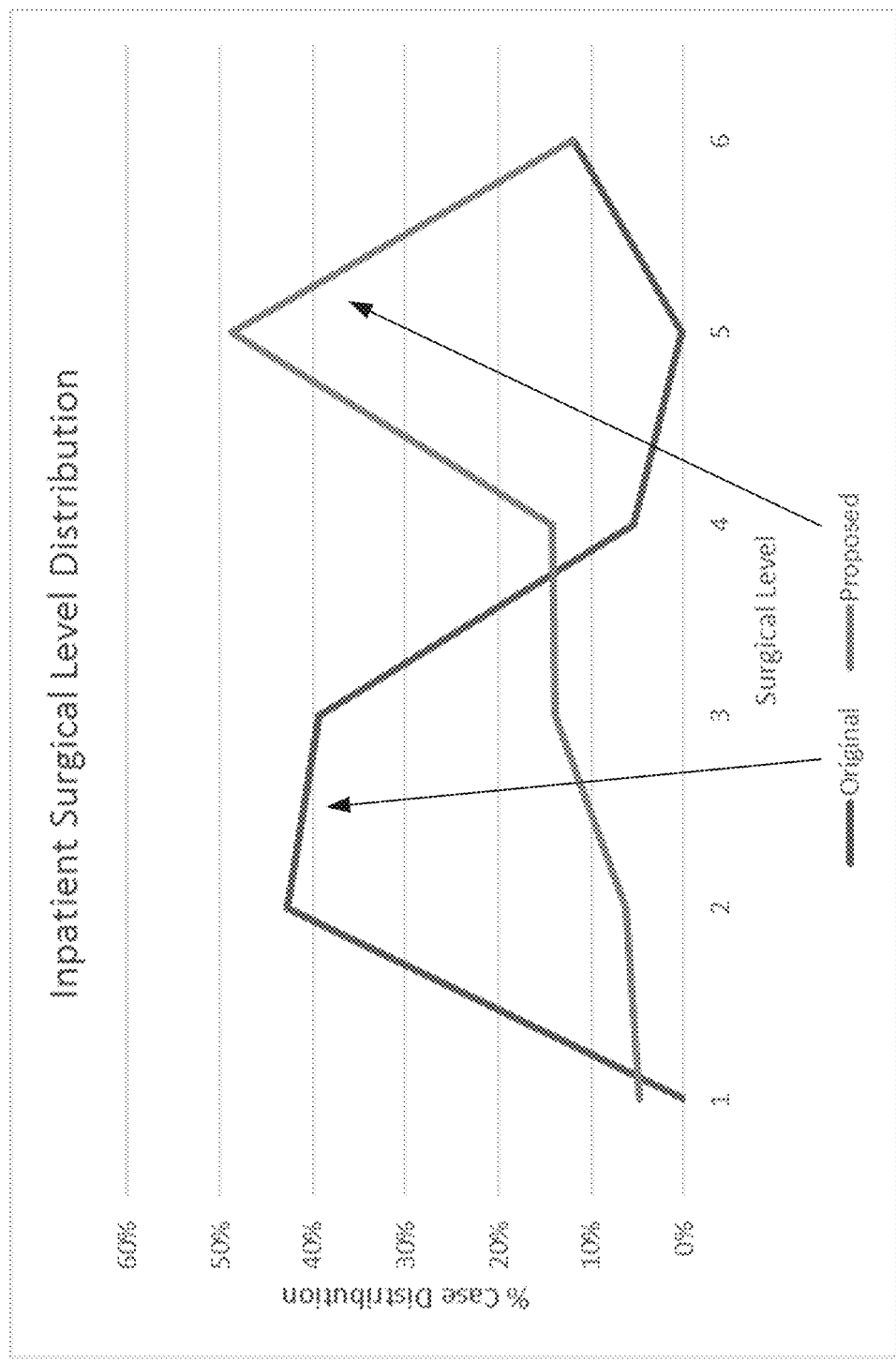
FIG. 4A is a graphical representation of an example of a data distribution for in-patient surgical procedures plotted on a level-by-level basis.
Figure 4B:
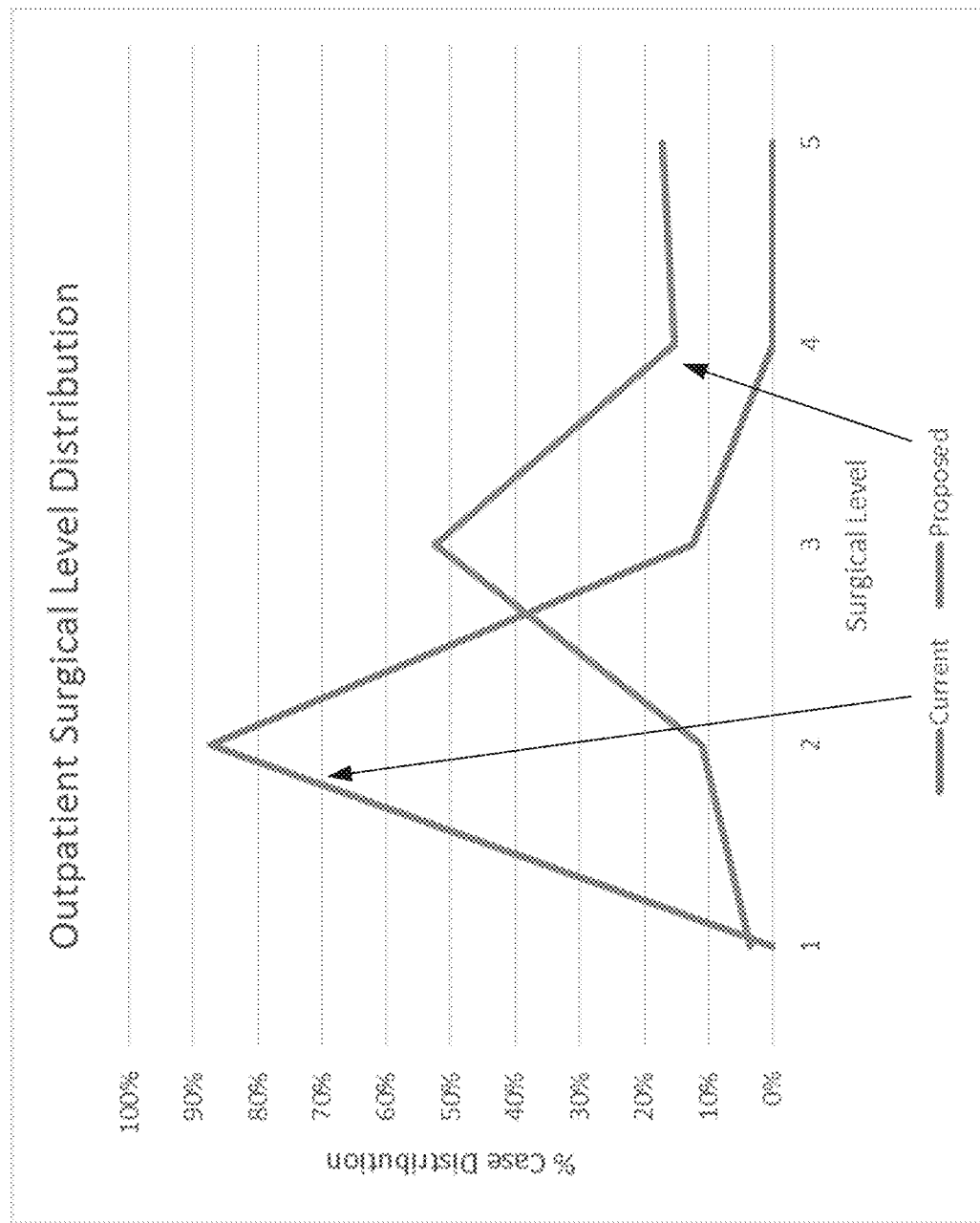
FIG. 4B is a graphical representation of an example of a data distribution for out-patient surgical procedures plotted on a level-by-level basis.
Figure 4C:
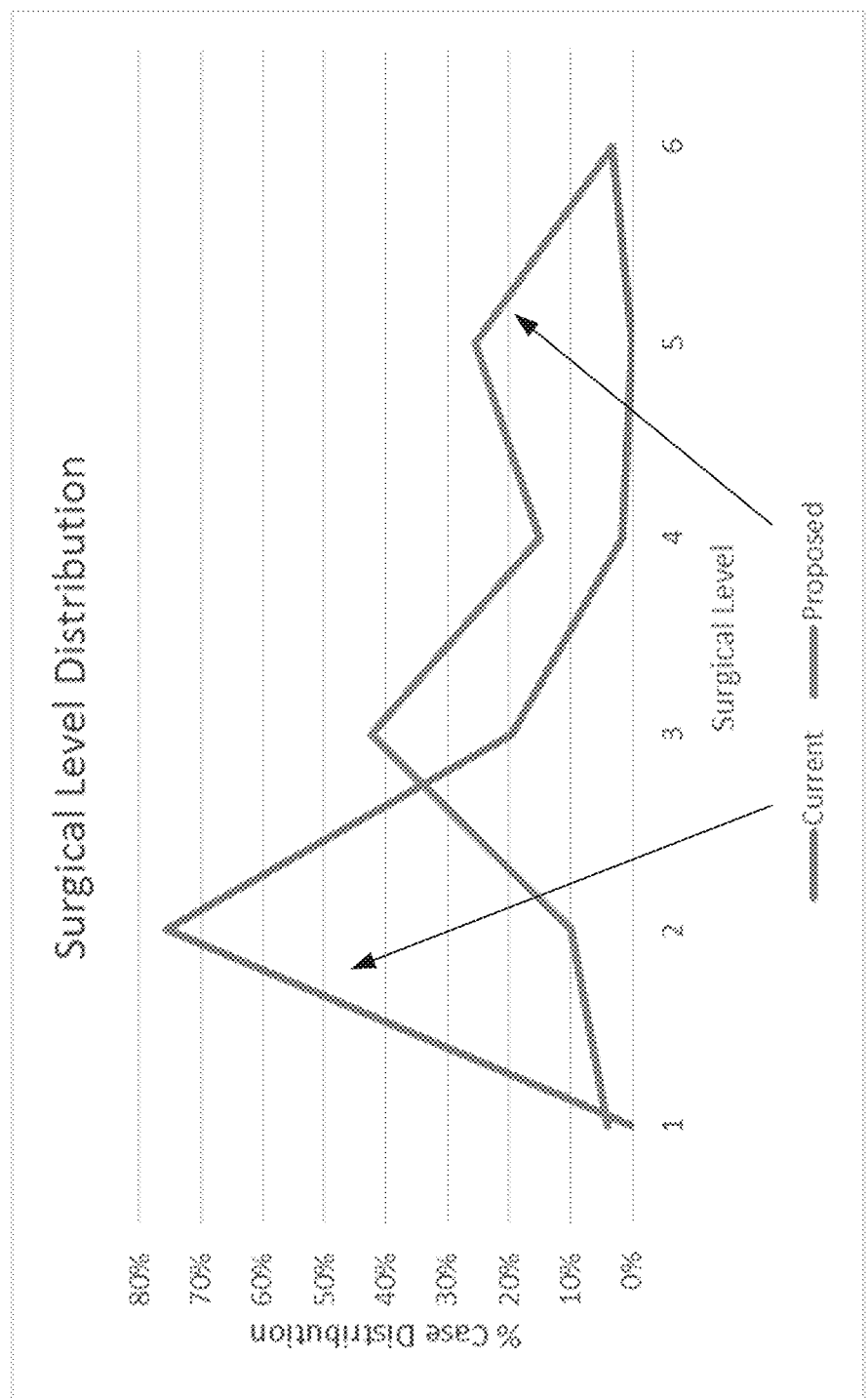
FIG. 4C is a graphical representation combining data from FIGS. 4A and 4B to depict an overall data distribution for in-patient and out-patient surgical procedures plotted on a level-by-level basis.

If the data distribution is not desirable, then one or more types of adjustments may be made at step 308, such as adjusting one or more relative weight cutoff points. The process then iteratively proceeds back to step 302. However, if the data distribution is desirable, then a determination can be made at step 310 whether the chosen classification meets a predetermined financial target. Such financial targets may be determined based on net revenue data or gross revenue data for the healthcare entity, for example. If the financial target is not met, then the process continues to step 308 where one or more adjustments can be made, such as adjusting surgical level prices, for example. The process then iteratively proceeds back to step 302. However, if the financial target is met at step 310, then the data distribution can be output at step 312 as a graphical element, for example. FIGS. 4A-4C include examples of graphical elements that illustrate percentage of case distribution for the population of medical procedures by surgical level. It can be seen that both original or current state distributions (i.e., before the inventive algorithm has been employed) and proposed distributions (i.e., after the inventive algorithm has been employed) are shown in these graphical displays for comparative purposes.

Figure 5:
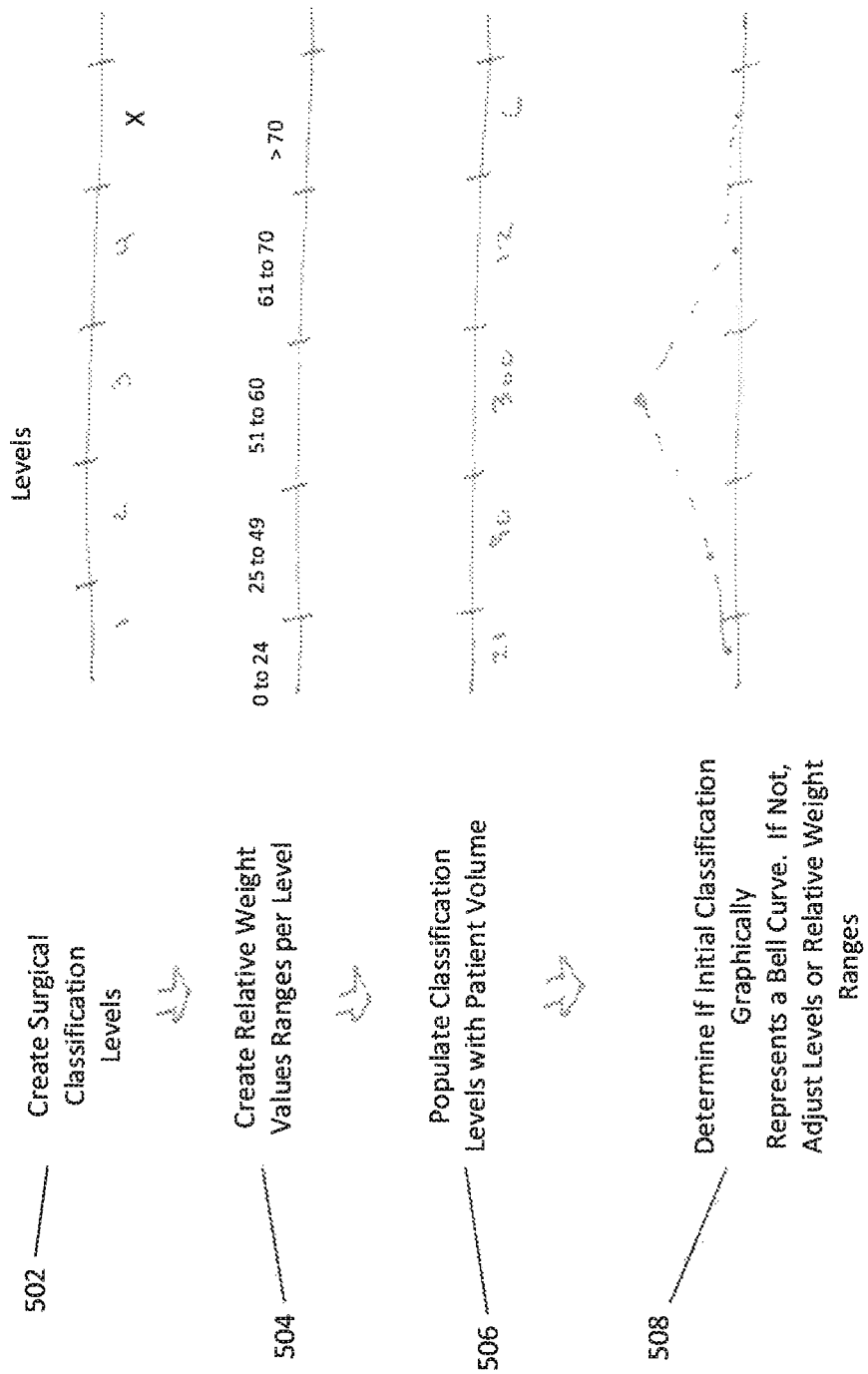
FIG. 5 is a process flow diagram illustrating one example of a process for restructuring and reclassifying medical procedure charges in accordance with certain embodiments of the invention.

In another example of a process flow involving the tools provided herein, and with reference to FIG. 5, the algorithm may be used to analyze data for a predetermined time period (e.g., twelve months) related to operating room claims data for inpatient and outpatient surgical cases of a medical facility. At step 502, multiple surgical classification levels can be determined based on analysis of the collected data. At step 504, the surgical levels associated with the surgical procedures can then be reclassified using the Medicare APC relative weight scheme, for example. At step 506, the classification levels can be populated with patient or procedure volume data, as shown. At step 508, it can be determined whether the initial classification graphically represents a bell curve, for example, or another statistically acceptable graphical representation of the analyzed data. If not, then either the surgical classification levels and/or the relative weight ranges can be adjusted at step 508. The graph can be generated again to determine whether or not the data graphically represents a bell curve or another statistically acceptable graphical representation of the analyzed data. It can be seen that this process can be performed iteratively and the data re-graphed until an acceptable result is obtained.

In connection with the process flow shown in FIG. 5, expected reimbursements can be modeled that reflect payment terms specific to the medical facility and payor mix, for example, among other potential factors. Then, multiple scenarios can be modeled to illustrate gross revenue and gross net revenue impact for the medical facility consistent with a desired financial target determined by the medical facility.

Figure 6:
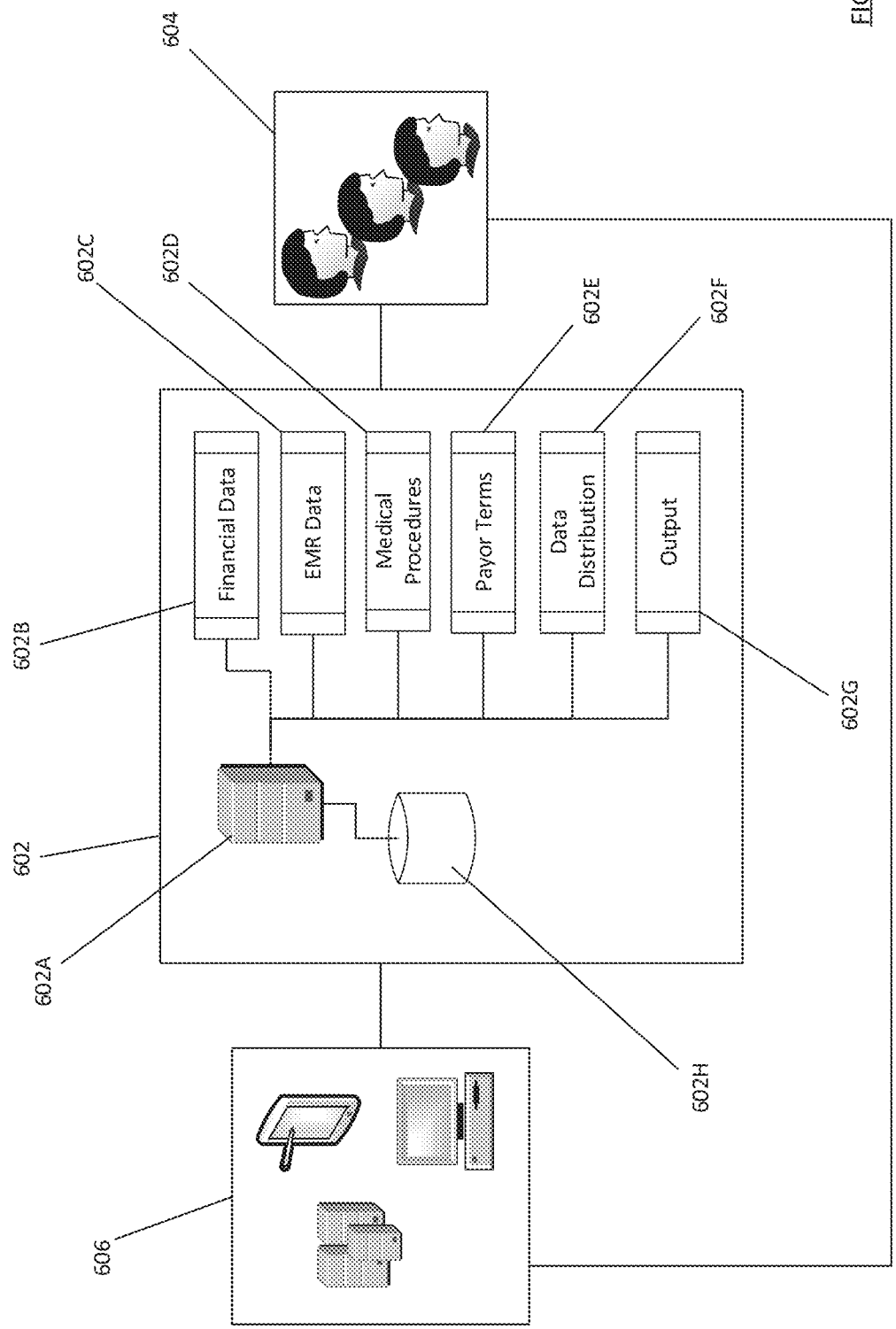
FIG. 6 schematically represents an example of a computer system architecture configured for executing various aspects of the processes, algorithms, and systems described herein.

FIG. 6 depicts an example of a computer system architecture structured for implementation of certain embodiments of the present invention. As shown, a medical procedure analysis system 602 can be programmed to perform analysis of charges associated with different medical procedures and can be made accessible by different users 604. The system 602 may include an electronic computer processor 602A programmed to execute various computer-based functions or tasks within the system, including the functions of various modules 602B-602G. For example, a financial data module 602B may be programmed to receive various types of financial data 102. An EMR data module 602C may be programmed to receive and process different kinds of EMR data 104. A medical procedures module 602D may be programmed to receive and process clinical procedure data 106, for example. In addition, a payor terms module 602E can be provided for receiving manual data input related to payor reimbursement terms 108, for example. A data distribution module 602F can be programmed to execute various tasks related to iteratively generating data distributions associated with medical procedure data, for example. An output module 602G may be provided to assist users with creation and modification that display various types of output elements, such as graphs, charts, or tables comparing original and proposed distributions, for example. Table outputs can be generated, for example, which display the recommended surgical level assigned to each medical procedure code, comparing the original default level to the proposed new level. In various embodiments, one or more data storage media 602H may be provided for storing documents, files, data, or other content shared or uploaded to the system 602.

In various embodiments, users 606 may access the system 602 with a variety of access devices such as mobile devices, tablets, laptops, desktops, or many other kinds of computing devices. It can be appreciated that such access devices, particularly mobile devices, may need to be programmed for secure communications to resist transmission or improper interception of personal healthcare information (PHI) of a user 606, for example. In other embodiments, devices such as mobile devices and tablets may not be permitted for use with the system 602. In certain embodiments, the system 602 may receive information from one or more external data sources or computer systems 606. Examples of such external data sources 606 include healthcare data systems, third party modules, patient registration data systems, patient claims data systems, and patient surgical data systems, among many others.

Figure 7:
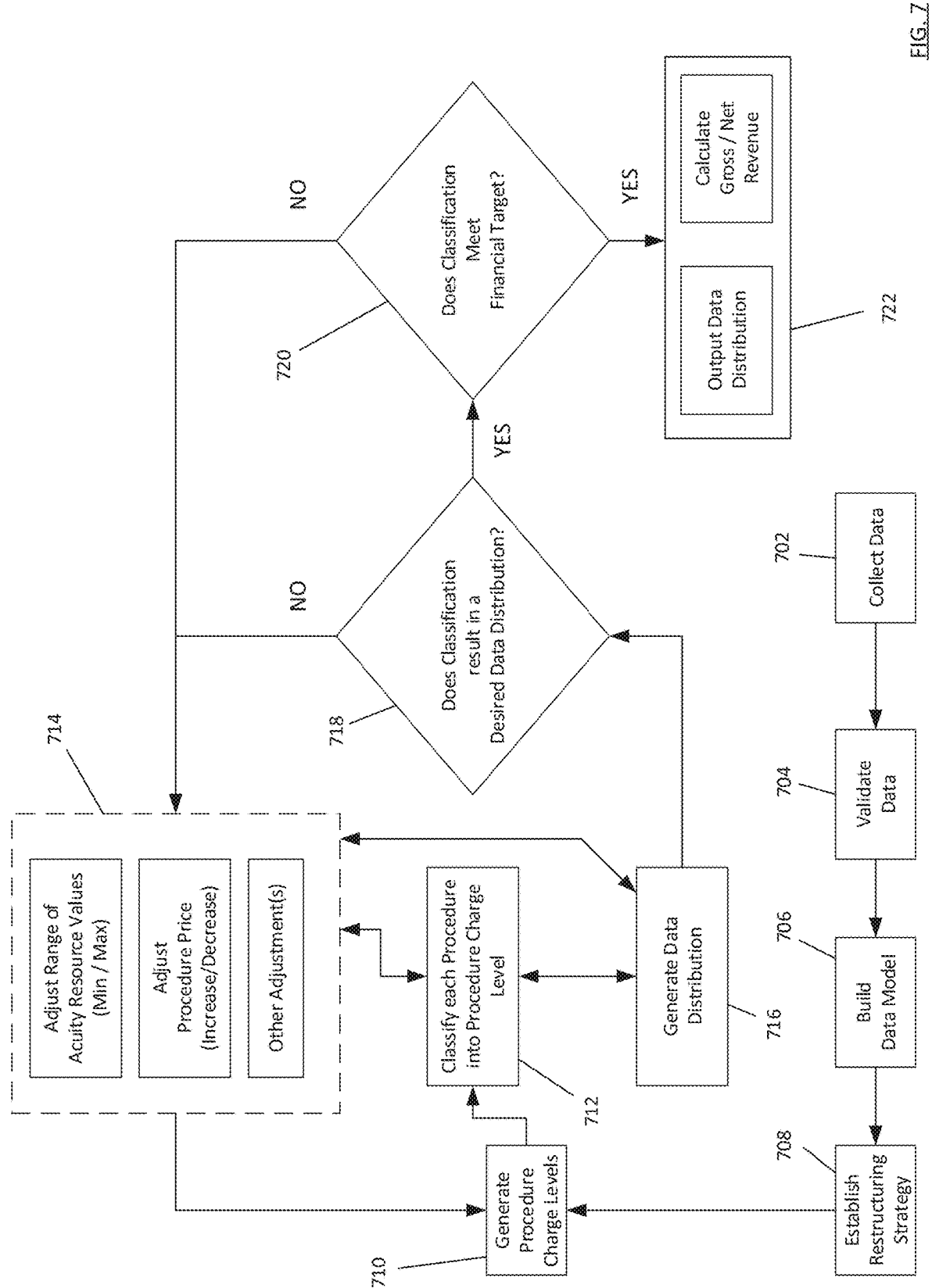
FIG. 7 is a process flow diagram illustrating one example of a process for restructuring and reclassifying medical procedure charges in accordance with certain embodiments of the invention.

FIG. 7 illustrates another example of a process flow for analyzing, restructuring, and controlling the charge process associated with performing different medical procedures. This process flow may be executed consistent with different aspects of the techniques, processes, and computer systems described herein.

In this example, data associated with medical procedures can be collected at step 702 by the system 602. Such data and related information may include, for example and without limitation, historical surgical logs; claim charge details; payor name/plan name and account class information; healthcare information management (HIM) coded Healthcare Common Procedure Coding System (HCPCS) codes, CPT codes for outpatient encounters, and DRG codes for inpatient encounters; Medicare Wage Index and top (e.g., three to five) payor commercial contracts; 837 claims data; 835 payment remittance data; and/or current surgical procedure listing data along with current level assignment, if any. FIG. 8 illustrates an example of collected medical procedure data in which a surgical procedure has a total procedure charge that is below the reimbursement rate associated with the surgical procedure, and for which charge restructuring may be appropriate.

The collected medical procedure data can then be validated at step 704 by reviewing the collected data to confirm various characteristics of the data set. For example, validation may involve verifying that a sufficiently complete and accurate set of records has been collected to depict a predetermined historical time period (e.g., 12 months). Validation may also include checking for duplication of records or gaps in the data records, which could skew the historical accuracy of the data. The validation process may also include confirming that unique identifiers exist among the separate data files, which will facilitate appropriately connecting the data to re-create an accurate patient surgical encounter, along with the associated expected reimbursement, patient bill and actual payment information, for example. In certain embodiments, as part of developing and creating a reimbursement model, payor contract information can be collected, for example, and expected reimbursement information can be applied to each medical procedure.

At step 706, a data model can be built which includes a unique record for all patient encounters or medical procedures (e.g., surgical procedures) performed within the predetermined time frame. One step associated with building the data model is to recreate the baseline charge, normalize the charges based on standard charge amounts for each encounter included in a given data set. By doing this baseline assessment, recommended variations to the current charge structure can be measured accurately in comparison to baseline data. The baseline data incorporated into the data model for each encounter may include a combination of data selected from, for example and without limitation: hospital location; patient insurance name/ID; procedure ID; procedure name; inpatient/outpatient status; CPT(s) reported for case; CPT description; Medicare APC relative weight associated with each CPT assigned to case; DRG associated with case; total encounter charge; surgical length of case (e.g., in minutes); recovery time (e.g., in minutes); anesthesia time (e.g., in minutes); current level or acuity assignment (if any); total charges broken out by revenue code groups (e.g., 360-1, 710, 370, 27x, or all other); expected reimbursement associated with each encounter, perhaps specific to patient; insurance name/ID, if available; maximum expected reimbursement, based on payor contracts; collected amount, for each encounter, regardless of patient insurance name/ID; and/or actual payment amount for each encounter.

At step 708, baseline charges for medical procedures can be analyzed to establish a restructuring strategy for the current charge structure. Baseline medical procedure charge data can be checked against modeled or expected reimbursement rate data to identify where charges might be significantly higher or lower than the expected reimbursement rates. Also, payment data can be compared to expected reimbursement to identify historical underpayments. In addition, charges can be evaluated against relative weight data to identify if the acuity designation sufficiently aligns with the gross charge to the patient for all or a predetermined portion of encounters in the data set.

At step 710, the collected data can be categorized in connection with a predetermined number of procedure charge levels as shown in the example tabulations of FIGS. 9 and 10. FIG. 9 includes an example of a current structure for a given medical procedure; and FIG. 10 illustrates an example of a newly proposed structure for the same procedure. It can be appreciated that each charge level may be associated with a range of APC relative weights, for example. Medical procedures can be assigned to an appropriate charge level, at step 712, in accordance with one or more level assignment rules. In one example of a level assignment rule, for out-patient procedures and procedures that can be performed in both in-patient out-patient settings, APC relative weight data can be retrieved and charge level assigned based on a recommended procedure level. In another example, for in-patient only procedures (e.g., with status indicator=C, and for which an APC relative weight does not exist), the procedure can be assigned to the highest procedure charge level. Alternatively, another rule might involve using CPT and ICD-10 procedure codes to look up all DRGs applicable to the ICD-10 procedure codes, reviewing and identifying DRGs with descriptions similar to the procedure name, and then applying the maximum DRG to assign the procedure level based on the DRG weight range. FIG. 11 illustrates an example of changing procedure charge levels for various medical procedures. FIG. 12 provides a tabulation of average charges by level, comparing current charges under an existing structure with proposed charges under a new structure.

Prices can be assigned to each newly created procedure charge level at step 714 using prices that are consistent with the restructuring strategy established during the baseline charge analysis at step 708. In various embodiments, a pricing factor or adjustment may be applied to each procedure in one or more of the following scenarios, for example and without limitation: procedure charges exceed maximum reimbursement rates; procedure charges align with relative weight acuity (e.g., a procedure with a higher relative weight may have a correspondingly higher charge); and/or gross revenue variance on procedure charges meet a predetermined target level at a given price point. In certain embodiments, gross revenue variance can be calculated for the newly proposed procedure level assignments to confirm or adjust prices as needed. The difference between each newly proposed surgical charge and each current surgical charge, for example, can be calculated for all encounters in the data model. The sum total of these gross revenue variances can be calculated for all encounters and then compared to the baseline gross revenue charges (i.e., the sum of all baseline encounters). This calculated gross revenue variance can be a percentage value, for example, which compares the prior or current gross revenue value to the new gross revenue value under the proposed charge structure.

Among other functions that can be performed at step 714, one or more minima or maxima of the relative weight ranges (see, e.g., FIG. 8) can be adjusted, such that the in-patient and out-patient total volume distribution is within tolerance limits of a desired data distribution (e.g., a bell curve). Processing at this step may involve calculating a total number of surgical cases, for example, that fall into each procedure charge level. The process can then calculate each sum of encounters or number of patients by level, and then represent this calculation as a percentage of the total overall surgical encounters. This distribution of values can be displayed as a line graph at step 716 (or another kind of graphical representation) and then reviewed to determine if volume distribution represents a desired statistical distribution (e.g., a bell curve) at step 718. Also, relative weight ranges may be adjusted at step 714 as needed to regenerate the data distribution at step 716, which can be displayed and assessed again (and for successive iterations as needed or desired) at step 718 to determine whether a desired data distribution has been achieved. FIG. 4C illustrates an example of a bell curve type desired data distribution for surgical procedures.

At step 720, the process attempts to determine if a proposed charge structure meets predetermined financial targets and strategy. For example, with prices set for each level, the new structure can be reviewed to determine if targeted financial expectations have been met. Do all proposed procedure charges exceed reimbursement rates associated with those procedures? Do the procedure charges align with relative weight acuity? Does the gross revenue variance compared between baseline and proposed procedure charges align with the strategy developed at step 708? If the targeted financial expectations are not met, then processing may return to step 714 for execution of a price adjustment, or other adjustments as needed to meet the expectations.

At step 722, the desired data distribution can be output to a display, for example, in the form of a suitable a graphical representation (e.g., a line graph). Also, a net revenue variance can be calculated, such as for surgical procedures in a hospital setting. In one aspect of this calculation, for encounters where a baseline charge falls below payor specific reimbursement, and the proposed charge is greater than baseline surgical charge, and the proposed surgical charge is greater than the payor specific reimbursement, then the difference between payor specific reimbursement and baseline surgical charge can be calculated. In another aspect of this calculation, for encounters where the baseline charge falls below the payor specific reimbursement, and the proposed surgical charge is greater than the baseline surgical charge, and the proposed surgical charge is less than the payor specific reimbursement, then the difference between proposed surgical charge and the baseline surgical charge can be calculated. Also, for encounters where the payor reimburses as percentage of the charge, the difference between the proposed surgical charge and the baseline surgical charge can be calculated and multiplied by the reimbursement percentage. The sum for all encounters can then be calculated to obtain the total net revenue variance. For example, the table shown in the example of FIG. 13A illustrates comparison values and impact on gross and net revenue, for example, in a first scenario with no price change. In another example, FIG. 13B illustrates another scenario showing the effect of a 1% price increase for operating room level charges.

In various other data modeling aspects of the present invention, when multiple CPTs have been coded for the same encounter, the CPT with the highest APC relative weight can be set as the primary CPT. When multiple procedures have been performed in the same surgical operation, for example, the procedure with the highest default level can be set as the primary procedure. Also, for each procedure code, the level charge can be assigned based on the most frequently populated recommended level, which may be based on the relative value of the primary CPT. For similar medical procedures, the same procedure charge level can be assigned for both out-patient and in-patient procedures where an APC relative weight exists.

The examples presented herein are intended to illustrate potential and specific implementations of the present invention. It can be appreciated that the examples are intended primarily for purposes of illustration of the invention for those skilled in the art. No particular aspect or aspects of the examples are necessarily intended to limit the scope of the present invention. For example, no particular feature of the examples of system architectures, configurations, data definitions, or process flows described herein are necessarily intended to limit the scope of the invention, unless such feature is specifically recited in the claims.

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that a sufficient understanding of the present invention can be gained by the present disclosure, and therefore, a more detailed description of such elements is not provided herein.

Any element expressed herein as a means for performing a specified function is intended to encompass any way of performing that function including, for example, a combination of elements that performs that function. Furthermore, the invention, as may be defined by such means-plus-function claims, resides in the fact that the functionalities provided by the various recited means are combined and brought together in a manner as defined by the appended claims. Therefore, any means that can provide such functionalities may be considered equivalents to the means shown herein.

In various embodiments, various models or platforms can be used to practice certain aspects of the invention. For example, software-as-a-service (SaaS) models or application service provider (ASP) models may be employed as software application delivery models to communicate software applications to clients or other users. Such software applications can be downloaded through an Internet connection, for example, and operated either independently (e.g., downloaded to a laptop or desktop computer system) or through a third-party service provider (e.g., accessed through a third-party web site). In addition, cloud computing techniques may be employed in connection with various embodiments of the invention.

Moreover, the processes associated with the present embodiments may be executed by programmable equipment, such as computers. Software or other sets of instructions that may be employed to cause programmable equipment to execute the processes may be stored in any storage device, such as a computer system (non-volatile) memory. Furthermore, some of the processes may be programmed when the computer system is manufactured or via a computer-readable memory storage medium.

It can also be appreciated that certain process aspects described herein may be performed using instructions stored on a computer-readable memory medium or media that direct a computer or computer system to perform process steps. A computer-readable medium may include, for example, memory devices such as diskettes, compact discs of both read-only and read/write varieties, optical disk drives, and hard disk drives. A computer-readable medium may also include memory storage that may be physical, virtual, permanent, temporary, semi-permanent and/or semi-temporary. Memory and/or storage components may be implemented using any computer-readable media capable of storing data such as volatile or non-volatile memory, removable or non-removable memory, erasable or non-erasable memory, writeable or re-writeable memory, and so forth. Examples of computer-readable storage media may include, without limitation, RAM, dynamic RAM (DRAM), Double-Data-Rate DRAM (DDRAM), synchronous DRAM (SDRAM), static RAM (SRAM), read-only memory (ROM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory, ovonic memory, ferroelectric memory, silicon-oxide-nitride-oxide-silicon (SONOS) memory, magnetic or optical cards, or any other type of media suitable for storing information.

A "computer," "computer system," "computing apparatus," "component," or "computer processor" may be, for example and without limitation, a processor, microcomputer, minicomputer, server, mainframe, laptop, personal data assistant (PDA), wireless e-mail device, smart phone, mobile phone, electronic tablet, cellular phone, pager, fax machine, scanner, or any other programmable device or computer apparatus configured to transmit, process, and/or receive data. Computer systems and computer-based devices disclosed herein may include memory and/or storage components for storing certain software applications used in obtaining, processing, and communicating information. It can be appreciated that such memory may be internal or external with respect to operation of the disclosed embodiments. In various embodiments, a "host," "engine," "loader," "filter," "platform," or "component" may include various computers or computer systems, or may include a reasonable combination of software, firmware, and/or hardware. In certain embodiments, a "module" may include software, firmware, hardware, or any reasonable combination thereof.

In various embodiments of the present invention, a single component may be replaced by multiple components, and multiple components may be replaced by a single component, to perform a given function or functions. Except where such substitution would not be operative to practice embodiments of the present invention, such substitution is within the scope of the present invention. Any of the servers described herein, for example, may be replaced by a "server farm" or other grouping of networked servers (e.g., a group of server blades) that are located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand, and/or providing backup contingency in the event of component failure or reduction in operability.

In general, it will be apparent to one of ordinary skill in the art that various embodiments described herein, or components or parts thereof, may be implemented in many different embodiments of software, firmware, and/or hardware, or modules thereof. The software code or specialized control hardware used to implement some of the present embodiments is not limiting of the present invention. For example, the embodiments described hereinabove may be implemented in computer software using any suitable computer programming language such as .NET or HTML using, for example, conventional or object-oriented techniques. Programming languages for computer software and other computer-implemented instructions may be translated into machine language by a compiler or an assembler before execution and/or may be translated directly at run time by an interpreter. Examples of assembly languages include ARM, MIPS, and x86; examples of high-level languages include Ada, BASIC, C, C++, C#, COBOL, Fortran, Java, Lisp, Pascal, Object Pascal; and examples of scripting languages include Bourne script, JavaScript, Python, Ruby, PHP, and Perl. Various embodiments may be employed in a Lotus Notes environment, for example. Such software may be stored on any type of suitable computer-readable medium or media such as, for example, a magnetic or optical storage medium.

Various embodiments of the systems and methods described herein may employ one or more electronic computer networks to promote communication among different components, transfer data, or to share resources and information. Such computer networks can be classified according to the hardware and software technology that is used to interconnect the devices in the network, such as optical fiber, Ethernet, wireless LAN, HomePNA, power line communication or G.hn. The computer networks may also be embodied as one or more of the following types of networks: local area network (LAN); metropolitan area network (MAN); wide area network (WAN); virtual private network (VPN); storage area network (SAN); or global area network (GAN), among other network varieties.

For example, a WAN computer network may cover a broad area by linking communications across metropolitan, regional, or national boundaries. The network may use routers and/or public communication links. One type of data communication network may cover a relatively broad geographic area (e.g., city-to-city or country-to-country) which uses transmission facilities provided by common carriers, such as telephone service providers. In another example, a GAN computer network may support mobile communications across multiple wireless LANs or satellite networks. In another example, a VPN computer network may include links between nodes carried by open connections or virtual circuits in another network (e.g., the Internet) instead of by physical wires. The link-layer protocols of the VPN can be tunneled through the other network. One VPN application can promote secure communications through the Internet. The VPN can also be used to separately and securely conduct the traffic of different user communities over an underlying network. The VPN may provide users with the virtual experience of accessing the network through an IP address location other than the actual IP address which connects the access device to the network. The computer network may be characterized based on functional relationships among the elements or components of the network, such as active networking, client-server, or peer-to-peer functional architecture. The computer network may be classified according to network topology, such as bus network, star network, ring network, mesh network, star-bus network, or hierarchical topology network, for example. The computer network may also be classified based on the method employed for data communication, such as digital and analog networks.

Embodiments of the methods and systems described herein may employ internetworking for connecting two or more distinct electronic computer networks or network segments through a common routing technology. The type of internetwork employed may depend on administration and/or participation in the internetwork. Non-limiting examples of internetworks include intranet, extranet, and Internet. Intranets and extranets may or may not have connections to the Internet. If connected to the Internet, the intranet or extranet may be protected with appropriate authentication technology or other security measures. As applied herein, an intranet can be a group of networks which employ Internet Protocol, web browsers and/or file transfer applications, under common control by an administrative entity. Such an administrative entity could restrict access to the intranet to only authorized users, for example, or another internal network of an organization or commercial entity. As applied herein, an extranet may include a network or internetwork generally limited to a primary organization or entity, but which also has limited connections to the networks of one or more other trusted organizations or entities (e.g., customers of an entity may be given access an intranet of the entity thereby creating an extranet).

Computer networks may include hardware elements to interconnect network nodes, such as network interface cards (NICs) or Ethernet cards, repeaters, bridges, hubs, switches, routers, and other like components. Such elements may be physically wired for communication and/or data connections may be provided with microwave links (e.g., IEEE 802.12) or fiber optics, for example. A network card, network adapter or NIC can be designed to allow computers to communicate over the computer network by providing physical access to a network and an addressing system through the use of MAC addresses, for example. A repeater can be embodied as an electronic device that receives and retransmits a communicated signal at a boosted power level to allow the signal to cover a telecommunication distance with reduced degradation. A network bridge can be configured to connect multiple network segments at the data link layer of a computer network while learning which addresses can be reached through which specific ports of the network. In the network, the bridge may associate a port with an address and then send traffic for that address only to that port. In various embodiments, local bridges may be employed to directly connect local area networks (LANs); remote bridges can be used to create a wide area network (WAN) link between LANs; and/or, wireless bridges can be used to connect LANs and/or to connect remote stations to LANs.

As employed herein, an application server may be a server that hosts an API to expose business logic and business processes for use by other applications. Examples of application servers include J2EE or Java EE 5 application servers including WebSphere Application Server. Other examples include WebSphere Application Server Community Edition (IBM), Sybase Enterprise Application Server (Sybase Inc), WebLogic Server (BEA), JBoss (Red Hat), JRun (Adobe Systems), Apache Geronimo (Apache Software Foundation), Oracle OC4J (Oracle Corporation), Sun Java System Application Server (Sun Microsystems), and SAP Netweaver AS (ABAP/Java). Also, application servers may be provided in accordance with the .NET framework, including the Windows Communication Foundation, .NET Remoting, ADO.NET, and ASP.NET among several other components. For example, a Java Server Page (JSP) is a servlet that executes in a web container which is functionally equivalent to CGI scripts. JSPs can be used to create HTML pages by embedding references to the server logic within the page. The application servers may mainly serve web-based applications, while other servers can perform as session initiation protocol servers, for instance, or work with telephony networks. Specifications for enterprise application integration and service-oriented architecture can be designed to connect many different computer network elements. Such specifications include Business Application Programming Interface, Web Services Interoperability, and Java EE Connector Architecture.

Embodiments of the methods and systems described herein may divide functions between separate CPUs, creating a multiprocessing configuration. For example, multiprocessor and multi-core (multiple CPUs on a single integrated circuit) computer systems with co-processing capabilities may be employed. Also, multitasking may be employed as a computer processing technique to handle simultaneous execution of multiple computer programs.

Although some embodiments may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a general-purpose processor or application specific processor. The embodiments, however, are not limited in this context.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several aspects without departing from the scope of the present disclosure. Any recited method can be carried out in the order of events recited or in any other order which is logically possible.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

Certain embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, application program interface (API), exchanging messages, and so forth.

It will be appreciated that those skilled in the art will be able to devise various arrangements which, although not explicitly described or shown herein, embody the principles of the present disclosure and are comprised within the scope thereof. Furthermore, all examples and conditional language recited herein are principally intended to aid the reader in understanding the principles described in the present disclosure and the concepts contributed to furthering the art, and are to be construed as being without limitation to such specifically recited examples and conditions. Moreover, all statements herein reciting principles, aspects, and embodiments as well as specific examples thereof, are intended to encompass both structural and functional equivalents thereof. Additionally, it is intended that such equivalents comprise both currently known equivalents and equivalents developed in the future, i.e., any elements developed that perform the same function, regardless of structure. The scope of the present disclosure, therefore, is not intended to be limited to the exemplary aspects and aspects shown and described herein.

Although various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those of ordinary skill in the art and, consequently, are not described in detail herein.

The flow charts and methods described herein show the functionality and operation of various implementations. If embodied in software, each block, step, or action may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processing component in a computer system. If embodied in hardware, each block may represent a circuit or a number of interconnected circuits to implement the specified logical function(s).

Although the flow charts and methods described herein may describe a specific order of execution, it is understood that the order of execution may differ from that which is described. For example, the order of execution of two or more blocks or steps may be scrambled relative to the order described. Also, two or more blocks or steps may be executed concurrently or with partial concurrence. Further, in some embodiments, one or more of the blocks or steps may be skipped or omitted. It is understood that all such variations are within the scope of the present disclosure.

Reference to "one embodiment" or "an embodiment" means that a particular feature, structure, or characteristic described in connection with the embodiment is comprised in at least one embodiment. The appearances of the phrase "in one embodiment" or "in one aspect" in the specification are not necessarily all referring to the same embodiment. The terms "a" and "an" and "the" and similar referents used in the context of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as," "in the case," "by way of example") provided herein is intended merely to better illuminate the disclosed embodiments and does not pose a limitation on the scope otherwise claimed. No language in the specification should be construed as indicating any non-claimed element essential to the practice of the claimed subject matter. It is further noted that the claims may be drafted to exclude any optional element. As such, this statement is intended to serve as antecedent basis for use of such exclusive terminology as solely, only and the like in connection with the recitation of claim elements, or use of a negative limitation.

Groupings of alternative elements or embodiments disclosed herein are not to be construed as limitations. Each group member may be referred to and claimed individually or in any combination with other members of the group or other elements found herein. It is anticipated that one or more members of a group may be comprised in, or deleted from, a group for reasons of convenience and/or patentability.

While various embodiments of the invention have been described herein, it should be apparent, however, that various modifications, alterations and adaptations to those embodiments may occur to persons skilled in the art with the attainment of some or all of the advantages of the present invention. The disclosed embodiments are therefore intended to include all such modifications, alterations and adaptations without departing from the scope and spirit of the present invention as described and claimed herein.

The invention claimed is:

1. A computer-implemented method for restructuring classification of multiple medical procedures for a healthcare entity, the method comprising:
   connecting an electronic computer system having at least one data storage medium for data communication with multiple different data sources;
   aggregating, in a data storage medium of an electronic computer system, data derived from the multiple different data sources comprising:
      medical procedure data including data associated with multiple patient encounters associated with medical procedures performed on patients involving medical treatment or clinical procedures performed on the patients,
      electronic medical record data including at least one medical procedure related code,
      financial data including data elements associated with charges related to the multiple patient encounters,
      reimbursement data including data associated with payor contract terms for reimbursement, and
      data comprising at least one of historical surgical log data, claim charge detail data, payor name data, plan name data, account class data, Healthcare Common Procedure Coding System (HCPCS) code data, diagnosis related groups (DRG) code data, Medicare Wage Index data, and surgical procedure listing data;

creating, by a processor of the computer system, a data model with the aggregated medical procedure data;

wherein the computer system processor comprises a grouping of multiple networked servers employing load-balancing software and configured for:

distributing processing workload between or among individual servers of the grouping of multiple networked servers in association with processing the aggregated data and creating the data model, and expediting computing processes for the computer system by harnessing collective and cooperative power of the multiple networked servers;

generating, by the processor and in response to the data model, a predetermined number of procedure charge levels each in association with an acuity resource value range;

creating, by the processor, relative weight value ranges for each acuity resource value range associated with each procedure charge level;

reclassifying, by the processor, each of the medical procedures into one of the generated procedure charge levels in accordance with at least one level assignment rule;

determining, by the processor, whether a reclassified result falls within a predetermined desired data distribution, including determining whether a generated desired data distribution results in a statistical distribution of procedure charge levels that is substantially a bell curve distribution, including reclassifying the result, iteratively, until the reclassified result falls within the predetermined data distribution;

providing remote access to multiple access devices of multiple users to view or modify at least one of the predetermined number of procedure charge levels, at least one of the relative weight value ranges, or at least one of the level assignment rules;

displaying a graphical representation on a computer screen display associated with each access device of each user, the graphical representation structured for:
presenting a data distribution indicative of originally classified medical procedures,
presenting a data distribution indicative of the reclassified medical procedures, and
facilitating determining whether the reclassification of the medical procedures results in a predetermined desired data distribution;

storing at least a portion of the reclassified medical procedure data in the data storage medium of the processor; and performing a medical procedure on a patient in accordance with the reclassified medical procedure data.

2. The method of claim 1, further comprising analyzing at least one baseline charge for the medical procedures for establishing a restructuring strategy for a medical procedure charge structure.

3. The method of claim 2, further comprising comparing at least one baseline medical procedure charge against an expected reimbursement value to identify whether the baseline charge is a predetermined amount higher or lower than the expected reimbursement value.

4. The method of claim 1, further comprising determining iteratively, by the processor, whether the reclassification results in a predetermined desired data distribution after adjusting at least a portion of at least one acuity resource value range.

5. The method of claim 1, further comprising determining iteratively, by the processor, whether the reclassification results in a predetermined desired data distribution after adjusting at least one level assignment for at least one medical procedure.

6. The method of claim 1, further comprising outputting, by the processor and as a graphical element on an electronic computer screen, at least one data distribution associated with reclassification of the medical procedures.

7. The method of claim 1, further comprising determining whether the reclassification of the medical procedures results in meeting a predetermined financial target.

8. The method of claim 7, further comprising comparing a proposed procedure charge to a reimbursement rate associated with the procedure.

9. The method of claim 7, further comprising determining whether a gross revenue variance between at least one baseline procedure charge and at least one proposed procedure charge for a given medical procedure exceeds a predetermined level.

10. The method of claim 7, further comprising when the financial target is not met, adjusting at least one of a price or at least a portion of at least one acuity resource value range for at least one medical procedure.

11. A computer system for restructuring classification of multiple medical procedures for a healthcare entity, the system comprising:

an electronic computer system having an electronic computer processor and at least one data storage medium, the system structured for data communication with multiple different data sources;

the system programmed for aggregating, in the data storage medium of the electronic computer system, data derived from the multiple different data sources comprising:

medical procedure data including data associated with multiple patient encounters associated with medical procedures performed on patients involving medical treatment or clinical procedures performed on the patients;

electronic medical record data including at least one medical procedure related code;

financial data including data elements associated with charges related to the multiple patient encounters; and reimbursement data including data associated with payor contract terms for reimbursement; and data comprising historical surgical log data, claim charge detail data, payor name data, plan name data, account class data, Healthcare Common Procedure Coding System (HCPCS) code data, diagnosis related groups (DRG) code data, and surgical procedure listing data;

wherein the computer system processor comprises a grouping of multiple networked servers employing load-balancing software and configured for:

distributing processing workload between or among individual servers of the grouping of multiple networked servers in association with processing the aggregated data and creating the data model, and expediting computing processes for the computer system by harnessing collective and cooperative power of the multiple networked servers;

the system further programmed for:
> creating, by the processor, a data model with the received medical procedure data;
> generating, by the processor and in response to the data model, a predetermined number of procedure charge levels each in association with an acuity resource value range;
> creating, by the processor, relative weight value ranges for each acuity resource value range associated with each procedure charge level;
> reclassifying, by the processor, each of the medical procedures into one of the generated procedure charge levels in accordance with at least one level assignment rule;
> determining, by the processor, whether a reclassified result falls within a predetermined desired data distribution, including determining whether a generated desired data distribution results in a statistical distribution of procedure charge levels that is substantially a bell curve distribution wherein the reclassified result is reclassified, iteratively, until the result falls within the predetermined data distribution;
> providing, by the processor, remote access to multiple access devices of multiple users to view or modify at least one of the predetermined number of procedure charge levels, at least one of the relative weight value ranges, or at least one of the level assignment rules;
> displaying a graphical representation on a computer screen display of each access device of each user, the graphical representation structured for:
>> presenting a data distribution indicative of originally classified medical procedures, and
>> presenting a data distribution indicative of the reclassified medical procedures;
>
> storing at least a portion of the reclassified medical procedure data in the data storage medium of the processor;
> determining, by the processor, whether the reclassification of the medical procedures results in a predetermined desired data distribution; and
> communicating, by the processor, at least a portion of the reclassified medical procedure data in connection with performing a medical procedure on a patient in accordance with the reclassified medical procedure data.

12. The system of claim 11, further comprising analyzing at least one baseline charge for the medical procedures for establishing a restructuring strategy for a medical procedure charge structure.

13. The system of claim 12, further comprising comparing at least one baseline medical procedure charge against an expected reimbursement value to identify whether the baseline charge is a predetermined amount higher or lower than the expected reimbursement value.

14. The system of claim 11, further comprising determining iteratively, by the processor, whether the reclassification results in a predetermined desired data distribution after adjusting at least a portion of at least one acuity resource value range.

15. The system of claim 11, further comprising determining iteratively, by the processor, whether the reclassification results in a predetermined desired data distribution after adjusting at least one level assignment for at least one medical procedure.

16. The system of claim 11, further comprising outputting, by the processor and as a graphical element on an electronic computer screen, at least one data distribution associated with reclassification of the medical procedures.

17. The system of claim 11, further comprising determining whether the reclassification of the medical procedures results in meeting a predetermined financial target.

18. The system of claim 17, further comprising comparing a proposed procedure charge to a reimbursement rate associated with the procedure.

19. The system of claim 17, further comprising determining whether a gross revenue variance between at least one baseline procedure charge and at least one proposed procedure charge for a given medical procedure exceeds a predetermined level.

20. The system of claim 17, further comprising determining when the financial target is not met and adjusting at least one of a price or at least a portion of at least one acuity resource value range for at least one medical procedure.

* * * * *